United States Patent
Savard

(10) Patent No.: US 12,390,304 B2
(45) Date of Patent: Aug. 19, 2025

(54) METHOD FOR PROVIDING DENTAL ALIGNERS TO A SUBJECT SHOWING A NON-ALIGNEMENT OF ITS DENTITION

(71) Applicant: ORTHOIN3D, Paris (FR)

(72) Inventor: Brice Savard, Boulogne-Billancourt (FR)

(73) Assignee: ORTHOIN3D, Paris (FR)

(*) Notice: Subject to any disclaimer, the term of this patent is extended or adjusted under 35 U.S.C. 154(b) by 821 days.

(21) Appl. No.: 17/413,138

(22) PCT Filed: Dec. 13, 2019

(86) PCT No.: PCT/EP2019/085181
§ 371 (c)(1),
(2) Date: Jun. 11, 2021

(87) PCT Pub. No.: WO2020/120775
PCT Pub. Date: Jun. 18, 2020

(65) Prior Publication Data
US 2022/0061958 A1    Mar. 3, 2022

(30) Foreign Application Priority Data

Dec. 14, 2018  (EP) .................................... 18306697

(51) Int. Cl.

| | |
|---|---|
| *A61C 7/00* | (2006.01) |
| *A61C 7/08* | (2006.01) |
| *B33Y 50/00* | (2015.01) |
| *B33Y 80/00* | (2015.01) |
| *G16H 10/60* | (2018.01) |
| *G16H 30/20* | (2018.01) |
| *G16H 30/40* | (2018.01) |

(52) U.S. Cl.
CPC ................ *A61C 7/002* (2013.01); *A61C 7/08* (2013.01); *B33Y 50/00* (2014.12); *B33Y 80/00* (2014.12); *G16H 10/60* (2018.01); *G16H 30/20* (2018.01); *G16H 30/40* (2018.01)

(58) Field of Classification Search
None
See application file for complete search history.

(56) References Cited

U.S. PATENT DOCUMENTS

| | | | |
|---|---|---|---|
| 5,975,893 A | 11/1999 | Chishti et al. | |
| 2005/0048433 A1* | 3/2005 | Hilliard | A61C 7/00 433/24 |
| 2005/0192835 A1* | 9/2005 | Kuo | B33Y 50/00 705/2 |
| 2015/0132708 A1* | 5/2015 | Kuo | A61C 7/08 433/2 |
| 2017/0100213 A1* | 4/2017 | Kuo | G16H 20/40 |
| 2018/0280118 A1 | 10/2018 | Cramer | |
| 2020/0085546 A1* | 3/2020 | Li | A61C 13/34 |
| 2020/0315744 A1* | 10/2020 | Cramer | G16H 50/50 |
| 2021/0186659 A1* | 6/2021 | Li | G06T 17/20 |

FOREIGN PATENT DOCUMENTS

| | | |
|---|---|---|
| WO | 2008/024450 A1 | 2/2008 |
| WO | 2018153219 A1 | 8/2018 |

OTHER PUBLICATIONS

International Search Report issued on Jun. 23, 2020 in corresponding International Application No. PCT/EP2019/085181; 5 pages.

* cited by examiner

*Primary Examiner* — Nicholas D Lucchesi
(74) *Attorney, Agent, or Firm* — Maier & Maier, PLLC

(57) ABSTRACT

A personalized method for providing at least one dental aligner; the method being with reference to an actual state of the dentition of the patient and in view of an improvement plan of the alignment targeted over a period of time ranging from 1 to 16 weeks, of the teeth of a subject. The method includes the steps of: (i) providing a 2D image and/or 3D volume of the dentition of a subject showing a non-alignment of its dentition; (ii) recovering clinical markers of the subject; (iii) producing an initial set of manufacturing parameters of the at least one aligner; (iv) building up an image of the 1-16 weeks target of improvement; and (v) directly 3D printing of the at least one personalized aligner fitting with the predicted evolution of intermediate tooth displacement for each tooth of the patient during the improvement plan.

10 Claims, No Drawings

METHOD FOR PROVIDING DENTAL ALIGNERS TO A SUBJECT SHOWING A NON-ALIGNEMENT OF ITS DENTITION

FIELD

The present invention relates to the field of orthodontics. Especially, the present invention relates to a method for manufacturing dental aligner(s) for short or long orthodontic treatments, said aligner(s) being able to apply a displacement force suitable for each tooth in the dentition of a patient over the treatment period; said method including recovering clinical markers of the patients comprising the form and/or the size of each tooth (including the corresponding crown and/or root) of the dentition of the patient, producing an initial set of manufacturing parameters of the aligner(s), building up an image of few weeks of improvement, defining a final set of manufacturing parameters for the corresponding aligner(s) and using three-dimensional printing processes (3D).

BACKGROUND

Theoretically, the teeth are aligned in a horseshoe-shaped curve. However, for hereditary reasons, bad habits in childhood or with time and bone modifications due to aging, it happens that a shift of one or more teeth occurs with respect to this horseshoe curve.

Orthodontic treatment corrects these defects. To date, two treatment routes exist: either the braces system or the dental aligner system.

The system of braces consists of fixing on the wall of the teeth (buccal or lingual surface), elements held by a wire. This method of treatment, while effective, is relatively uncomfortable for the patient as this device is relatively unsightly, painful and unhygienic.

One of the possible alternatives is to use orthodontic aligners. Such aligner is in the form of a gutter and is placed on the teeth of the patient's lower and/or upper jaw. Aligners are more discreet and less painful than braces. Moreover, the teeth of the patient can easily be cleaned contrary to braces.

However, orthodontic treatment by wearing an aligner is much more expensive than the braces system because of its manufacturing process. In practice, the practitioner images the initial dentition of the patient, sends instructions to an operator who suggests an ideal end state in which the entire dentition is aligned in a horseshoe curve and has a set of aligners manufactured. As the operator is not an orthodontist, the ideal end state is obtained only after a large number of exchanges between the practitioner and the operator. The set of the manufactured aligners are supposed to fit each evolution of the teeth of the patient foreseen by the treatment plan.

However, this conventional process has drawbacks.

Since it is not possible for a practitioner to know precisely at the beginning of the treatment, how the dentition of the patient will respond to the wear of the aligner, in the set of the aligners, some of them do not match with the real state of the dentition of the patient and are useless. Indeed, over time, an offset between the shape of the aligner and the actual dentition of the patient may occur; for example, when one or more teeth do not move according to the simulation scheme. This discordance between the shape of the aligner and the actual dentition of the patient can cause pain in the teeth or temporomandibular joints, and may cause undesired parasitic movements resulting in the impossibility of wearing the corresponding aligners. Consequently, a new treatment plan has to be realized with the manufacture of a new set of aligners, which is a waste of time and money.

Furthermore, current aligners are manufactured by thermoforming over a positive tooth model that strongly limits the functionalization and the personalization of this intraoral device. For example, thermoformed aligners may comprise further manufacturing steps such as creating notches so that the patient can put inter-arch elastics. However, creating notches weakens the aligner. Another drawback of aligners obtained from thermoforming is the lack of homogenous thickness that may cause if the thickness is too low, an absence of applied force on the teeth and thus, a loss of efficiency of the thermoformed aligner. Moreover, thermoforming also limits the effectiveness of the aligners. Indeed, a number of cleats need to be added for non-optimal adaptation of the aligners on the teeth in order to express complex movements such as rotations and delusions. Conventional techniques of manufacturing aligners seem unsuited to the reality of the field, cause a waste of time for both the practitioner and the patient, and generates high costs.

There is therefore a need for a dental aligner manufacturing process to be more accurate than the conventional manufacturing methods. Especially, there is therefore a need for a dental aligner manufacturing a process more accurate in order to match the evolution of the dentition movement over time of a patient than conventional manufacturing methods. There is also a need for further personalizing the aligner with the clinical and anatomical features of the patient over time. There is also a need for providing a personalized method for providing an aligner, configured to learn during the treatment, depending how the patient reacts to be even more precise in the design of the aligner; in particular, regarding the suitable manufacturing parameters such as the targeted applied forces, the amounts of teeth displacement by aligner, the presence or not of auxiliaries on the aligner such as cleats. There is also a need for providing a personalized method for providing an aligner that can be modified during the treatment plan.

There is also a need for providing a dental aligner suitable to the dental disease and the dental and/or mandibular morphology of a patient. Especially, there is a need for providing a dental aligner comprising physical and/or chemical means for applying a force on each tooth of the dentition of a patient in order to efficiently move one or more teeth of this dentition, while reducing or deleting dental pain.

Advantageously, the dental aligner of the invention can apply a force on each tooth of the dentition of a patient in order to move one or more teeth according to a predetermined dental alignment improvement plan. Each applied force on a tooth in a same dentition, may be identical or different from another applied force on another tooth in this dentition.

Advantageously, the method for manufacturing the dental aligner of the invention allows determining the best physical and/or chemical parameters of the aligner for applying one or more forces on the dentition of a patent wearing the dental aligner; each tooth receiving at least one applied force for moving it; and said applied force being identical or different from the applied force received by another tooth in the same dentition.

SUMMARY

The present invention refers to a method for providing at least one dental aligner comprising means for applying a displacement force, identical or different, on each tooth of the dentition of a patient; said method being with reference to an actual state of the dentition of the patient and in view of an improvement plan of the alignment targeted over a period of time ranging from 1 to 16 weeks, of the teeth of a subject, said method comprising:

i. providing a 2D image and/or 3D volume of actual state of the dentition of a subject showing a non-alignment of its dentition;

ii. recovering clinical markers of the subject comprising the form and/or size of the dental root and/or the crown for each tooth of the dentition and optionally one or more of further clinical markers selected from age, sex, dental disease, and anatomical features;

iii. producing an initial set of manufacturing parameters of the at least one aligner from:

the image or the volume of the actual state of the dentition of the subject, and its comparison with the image or the volume of a previous state of the dentition of the subject and/or with the image or the volume of a predicted state of the dentition of the subject, the recovered clinical markers of step ii, and information issued from a database of patients having same or similar etiology of non-alignment, same or similar image or volume in a previous state, same or similar evolution of tooth displacement or response to the improvement plan, same or similar clinical markers and/or including the data of the subject obtained before those of step i;

iv. building up a 3D volume the improvement plan from the initial set of manufacturing parameters obtained from step iii, leading to a final set of manufacturing parameters of the at least one aligner for a treatment period ranging from 1 to 16 weeks, said final manufacturing parameters comprising:

a thickness ranging from more than 0 mm to 6 mm, preferably from 0.4 to 1.0 mm, a Shore hardness ranging from more than 0 to 100 Shore units, a surface condition selected from smooth surface, rough surface and surface comprising dental adhesion means, and/or a pressure zone applying a force ranging from more than 0 N·mm to 10 N·mm; and v. directly 3D printing of the at least one aligner.

According to one embodiment, the final manufacturing parameters further comprise:

an elastics modulus, determined by ASTM 638-2010, ranging from more than 0 to 2000 MPa, preferably from 500 MPa to 1900 MPa, more preferably ranging from 1000 to 1800 MPa;

a tensile strength at yield, determined by ASTM 638-2010, ranging from more than 0 to 200 MPa, preferably from 10 to 100 MPa, more preferably from 40 to 70 MPa;

an offset yield stress, determined by ASTM 638-2010, ranging greater than 10 MPa, preferably greater than 20 MPa, more preferably greater than 25 MPa;

an elongation percentage at break, determined by ASTM 638-2010, ranging from more than 0 to 500%, preferably from 10 to 250%, more preferably from 80 to 200%;

a flexural strength, determined by ISO 178, ranging from more than 0 to 200 MPa, preferably from 10 to 100 MPa, more preferably from 50 to 70 MPa;

a flexural modulus, determined by ISO 178, ranging from more than 0 to 2000 MPa, preferably from 500 MPa to 1900 MPa, more preferably ranging from 1200 to 1500 MPa.

a tear strength, determined by any methods and/or norms known by the skilled artisan, ranging from more than 0 to 200 MPa, preferably from 10 to 100 MPa, more preferably from 45 to 60 MPa;

an elastic Young modulus, determined by any methods and/or norms known by the skilled artisan, ranging from more than 0 to 3000 MPa, preferably from 500 MPa to 2500 MPa, more preferably ranging from 600 to 2000 MPa;

a hardness, determined by any methods and/or norms known by the skilled artisan, ranging from more than 0 to 200 MPa, preferably from 10 to 180 MPa, more preferably from 40 to 160 MPa, even more preferably ranging from 40 to 80 MPa; and/or a creep, determined by any methods and/or norms known by the skilled artisan, ranging from more than 0 to 1000 mm, preferably from 50 to 500 mm, more preferably from 120 to 400 mm.

According to one embodiment, the aligner is made of a biocompatible matter.

According to one embodiment, the aligner can reconstruct the shape of the tooth. According to one embodiment, when the patient misses one or more teeth, the aligner can reconstruct the shape of the tooth or teeth, preferably in transparent or tooth color. According to one embodiment, when the patient misses one or more teeth, 3D printing technique may provide aligner reconstructing the shape of the tooth or teeth, and this shape may evolve during the treatment.

According to one embodiment, the 2D image or 3D volume of the dentition of a subject is achieved by directly scanning the dentition of the subject or by scanning a positive or a negative mold of the dentition of the subject.

According to one embodiment, scanning is implemented by MRI scanner, X-ray machine or intra-oral scanner; preferably by intra-oral scanner.

According to one embodiment, the anatomical features are selected from jaw sizes, the alignment between the lower jaw and the upper jaw, the jaw density, teeth number, the tooth structure, and/or structure of teeth crown.

According to one embodiment, the clinical markers further include the bone density of the dentition of the patient. According to one embodiment, the clinical markers further include the bone density of the dentition of the patient at the beginning and during the treatment.

According to one embodiment, producing an initial set of manufacturing parameters and/or building up an image the improvement plan, is(are) achieved by an algorithm, a deep learning software or a machine learning software.

According to one embodiment, the final manufacturing parameters of the at least one aligner further comprises one or more parameters selected from: the size, the density and/or the color of said aligner; from the temperature, the pressure, and/or the printing speed of the printing device; and/or from the nature, the viscosity and/or the amount of the printing ink.

According to one embodiment, 3D printing of the at least one aligner is achieved by stereolithography (SLA), fused deposition modeling (FDM), pellet additive manufacturing (PAM), digital light processing (DLP), continuous liquid interface production (CLIP), electron beam melting (EBM), binder jetting (BJ), laminated object manufacturing (LOM) or triple-jetting technology (PolyJet).

The present invention also concerns a dental aligner comprising means for applying a displacement force, identical or different, on each tooth of the dentition of a patient; said means comprising at least one active portion on the aligner; each active portion having:
- a thickness ranging from more than 0 mm to 6 mm, preferably from 0.4 to 1 mm,
- a Shore hardness ranging from more than 0 to 100 Shore units,
- a surface condition selected from smooth surface, rough surface and surface comprising dental adhesion means, and/or
- a pressure zone applying a force ranging from more than 0 N·mm to 10 N·mm.

According to one embodiment, the dental aligner of the invention comprises at least two different materials. According to one embodiment, the one active portion has:
- an elastics modulus, determined by ASTM 638-2010, ranging from more than 0 to 2000 MPa, preferably from 500 MPa to 1900 MPa, more preferably ranging from 1000 to 1800 MPa;
- a tensile strength at yield, determined by ASTM 638-2010, ranging from more than 0 to 200 MPa, preferably from 10 to 100 MPa, more preferably from 40 to 70 MPa;
- an offset yield stress, determined by ASTM 638-2010, greater than 10 MPa, preferably greater than 20 MPa, more preferably greater than 25 MPa;
- an elongation percentage at break, determined by ASTM 638-2010, ranging from more than 0 to 500%, preferably from 10 to 250%, more preferably from 80 to 200%;
- a flexural strength, determined by ISO 178, ranging from more than 0 to 200 MPa, preferably from 10 to 100 MPa, more preferably from 50 to 70 MPa;
- a flexural modulus, determined by ISO 178, ranging from more than 0 to 2000 MPa, preferably from 500 MPa to 1900 MPa, more preferably ranging from 1200 to 1500 MPa.
- a tear strength, determined by any methods and/or norms known by the skilled artisan, ranging from more than 0 to 200 MPa, preferably from 10 to 100 MPa, more preferably from 45 to 60 MPa;
- an elastic Young modulus, determined by any methods and/or norms known by the skilled artisan, ranging from more than 0 to 3000 MPa, preferably from 500 MPa to 2500 MPa, more preferably ranging from 600 to 2000 MPa;
- a hardness, determined by any methods and/or norms known by the skilled artisan, ranging from more than 0 to 200 MPa, preferably from 10 to 180 MPa, more preferably from 40 to 160 MPa, even more preferably ranging from 40 to 80 MPa; and/or
- a creep, determined by any methods and/or norms known by the skilled artisan, ranging from more than 0 to 1000 mm, preferably from 50 to 500 mm, more preferably from 120 to 400 mm.

According to one embodiment, the dental aligner of the invention is colored, preferably of the color of the dentition of the subject.

According to one embodiment, the dental aligner of the invention is transparent.

According to one embodiment, the applied force ranges from 0.0098 N·mm to 8 N·mm.

In the present invention, the following terms have the following meanings:

"About": preceding a figure means plus or less 10% of the value of said figure.

"Actual state of the dentition": refers to the physical and/or clinical characteristics of the dentition of a subject, such characteristics being defined and/or measured at the beginning of an improvement plan method. According to one embodiment, the actual state of the dentition takes into account previous evolution of the dentition such as for example resulting from a previous improvement plan of the alignment of dentition. According to one embodiment, the actual state of the dentition is defined by recovering clinical markers of the subject comprising the form and/or the size of each tooth of the dentition of the patient (such as the crown and/or the root) and/or by identifying the etiology of non-alignment of the dentition.

"Aligner": refers to a dental appliance in the form of a gutter, adapted to fit the dentition of the lower jaw and/or upper jaw of a subject and allowing a progressive movement of at least one tooth to the desired final position.

"Anatomical features": refers to any of the structural features characterizing the oral cavity of a subject. According to one embodiment, the expression "anatomical features" refers to the structural features characterizing the teeth and/or the jaws of a subject.

"Artificial intelligence" or "AI": refers to any of the device or computer program imitating or replacing human in certain implementation of his cognitive functions. According to one embodiment, AI is able to select relevant information in a database, for example a database of patients, and to analyze such relevant information in view of a question asked to the AI system and to provide to the questioner a relevant answer. According to one embodiment, AI is able to collect, update and select relevant information from one particular patient in a database in order to adapt manufacturing parameters of the at least one aligner to the actual state of the dentition of the patient. According to one embodiment, the expression "artificial intelligence" refers to an automated process. According to one embodiment, the artificial intelligence in the process of the invention compare the dental diagnostic of the patient $x_i$ to a database of patients $x_n$, preferably having same or similar etiology of non-alignment, same or similar image or, same or similar clinical markers; said database including or not the data of patient $x_i$.

"Binder jetting" or "BJ": refers to an additive manufacturing technique using binders sprayed onto powders to form a solid piece. The binders can be pigmented to add color to the final piece.

"Clinical markers": refers to information relative from the state of a subject comprising the form and/or the size of the dental root and/or the crown for each tooth of the dentition of a subject and optionally further including sex, age and/or anatomical features.

"Continuous liquid interface production": refers to an additive manufacturing technique using photo-polymerization to create solid objects of various shapes. According to one embodiment, the expression "continuous liquid interface production" refers to a 3D printing process comprising hardening a photosensitive polymer while the fabricated object is draw up out of the resin bath.

"Deep learning process": refers to a machine learning method based on artificial neural networks and/or artificial intelligence as defined above.

"Digital light processing" or "DLP": refers to an additive manufacturing technique using a projector to fix photopolymer. According to the invention, the expression "digital light processing" refers to a similar additive manufacturing technique which is SLA; DLP technique differs from SLA technique in the use of a light bulb instead of a UV laser beam.

"Electron beam melting" or "EBM": refers to an additive manufacturing technique using metal powder melting for manufacturing solid objects. In the EBM technique an electron beam is used for melting the metal powder, layer by layer. According to one embodiment, the temperature used in the EBM technique ranges from 700° C. to 1000° C. According to one embodiment, the EBM technique leads to solid objects with a high density, preferably from 50% to 100%. According to one embodiment, the EBM technique is implemented under vacuum.

"Etiology of a non-alignment of the dentition": refers to causes and factors resulting in at least one non-aligned tooth in the dentition of a patient.

"Fused deposition modeling (FDM)" or "fused filament deposition": refers to an additive manufacturing technique comprising a printing plate on which is printed the part, a filament coil which serves as printing material and an extrusion head also called extruder; said FDM technique comprising melting and extruding a filament which is then deposited layer by layer on the printing plate to gradually form the object.

"Laminated object manufacturing" or "LOM": refers to an additive manufacturing technique using a continuous sheet of material such as paper, plastic or metal; said sheets are successively glue together and cut to shape with a knife or a laser cutter.

"Machine learning method": refers to a set of algorithms and statistical models that computer systems use to perform a specific task without using explicit instructions According to one embodiment, the expression "machine learning method" deals with a set of algorithms and statistical models that act as an artificial intelligence as defined above. According to one embodiment, the expression "machine learning method" deals with a set of algorithms and statistical models which provide decisions or predicted solutions without being explicitly programmed to perform the task.

"MRI scanner" or "magnetic resonance imaging scanner": refers to a type of scan using a strong magnetic field and radio for providing detailed images of the organs and/or tissues within the body of a subject.

"Negative mold of an object": refers to a non-virtual, solid, three-dimensional representation of the inverse image of an object.

"Positive mold of an object": refers to a non-virtual, solid, three-dimensional accurate representation of an object.

"Pellet additive manufacturing" or "PAM": refers to an additive manufacturing technology starting from pellets of matter, preferably pellets of polymers, more preferably pellets of one or more thermoplastic polymers.

"Personalized method": refers to in the present invention, to a method that adapts to the specific characteristics of an individual and their evolution over time. Especially, the personalized method refers to a method that adapts to the different displacement rate for the teeth of a same subject.

"Predicted state of the dentition of a subject": refers to the state of the dentition of a subject, preferably who complies with a treatment plan, expected by the practitioner. According to one embodiment, the predicted or expected state of the dentition may be obtained either by using any algorithm, AI, deep learning method or machine learning method, by exploiting a database of patients and/or by using the previous data of said subject with similar clinical markers.

"Printing ink": refers to a liquid or a paste used in an additive manufacturing technique (or in 3D printing technique) for manufacturing solid objects. According to one embodiment, the printing ink comprises at least one polymer and/or monomer.

"Stereolithography" or "SLA": refers to an additive manufacturing technique using photopolymerization for manufacturing layer by layer, a solid object. In the SLA technique, a light-emitting device such as a laser, illuminates the transparent bottom of a tank filled with a liquid photopolymerizable resin that gradually solidifies; and in which the solidified resin is progressively dragged up by a lifting platform.

"Selective laser sintering" or "SLS": refers to an additive manufacturing technique whose principle is to heat by laser a powder such as plastics, glass and/or ceramics, for building the solid object. In SLS technique, the 3D printer places a thin layer of powder in its print ray, the laser heats the powder particles to form a section of the object. The print bin is then shifted slightly down of a layer thickness and the process is repeated until the object is finalized.

"Subject": refers to a warm-blooded animal, more preferably a human Preferably, the subject is a patient, i.e. the subject is awaiting the receipt of, or is receiving medical care or is/will be the object of a medical procedure.

"Triple jetting technology": refers to an additive manufacturing technique allows printing with three materials.

"3D-printing" or "additive manufacturing": refers to any process for manufacturing three-dimensional solid objects from a digital file.

"X-ray machine": refers to any machine involving X-rays. According to one embodiment, X-ray machine may be a machine for medical projectional radiography, machine for computed tomography, backscatter X-ray machines or detectors X-ray astronomy.

DETAILED DESCRIPTION

Personalized Method for Providing an Aligner

This invention relates to a method, preferably a personalized method, for providing a dental aligner. According to one embodiment, the method of the invention is for providing at least one dental aligner, preferably from 1 to 16 dental aligners, preferably from 1 to 12 dental aligners, preferably from 1 to 6 dental aligners, more preferably for providing one dental aligner each two weeks or for providing one dental aligner each three weeks. According to one embodiment, the method of the invention is for providing at least one dental aligner each week. According to one embodiment, the method of the invention is for providing a set of 1, 2, 3, 4, 5, 6, 7, 8, 9, 10, 11, 12, 13, 14, 15 or 16 dental aligners. According to one embodiment, the method of the invention is for providing a set of 1, 2, 3, 4, 5, 6, 7 or 8 dental aligners.

It is of course understood that the number of aligners is relative to the treatment of one arch. In the case of the treatment of two arches simultaneously, the number of aligners needed is doubled.

According to one embodiment, one aligner is worn less than 6 days, preferably less than 5 days. According to one embodiment, one aligner is worn during the night. According to one embodiment, depending on the manufacturing parameters of the aligner and/or the treatment plan of the invention resulting from the algorithm, the artificial intelligence, the deep learning process or the machine learning process, the aligner of the invention may be worn during 1, 2, 3, 4, 5, 6, 7, 8, 9, 10, 11, 12, 13, 14, 15 or 16 weeks.

According to one embodiment, depending on the manufacturing parameters of the aligner and/or the treatment plan of the invention resulting from the algorithm, the artificial intelligence, the deep learning process or the machine learning process, the aligner of the invention may be worn during the whole treatment period without needing the patient to change the aligner.

Personalized Method

According to one embodiment, the personalized method of the invention comprises reference to an actual, updated and/or current state of the dentition of a subject.

According to one embodiment, the method of the invention provides a personalized dental aligner, i.e. a dental aligner fitting with the current state of the dentition of a subject, and having specific manufacturing parameters for moving at least one tooth, preferably in a 1-16 weeks improvement plan, more preferably in a 3-16 weeks improvement plan, even more preferably in a 3-12 weeks improvement plan. According to one embodiment, the method of the invention provides a personalized dental aligner for moving teeth that must to be over the treatment period ranging from 1 to 16 weeks, that fits with the current state of the dentition of a subject and the displacement rate of each tooth in the dentition of the patient. According to one embodiment, the whole method of the invention is implemented in the dentist's office. According to one embodiment, the whole method of the invention is implemented during the dental visit. According to one embodiment, a part of the method of the invention is implemented at a care provider such as for example, by a care technician. According to one embodiment, the whole method of the invention is implemented by an orthodontist. According to one embodiment, a part of the method of the invention, preferably step (iii), is implemented by an orthodontist. According to one embodiment, the treatment plan of the invention is tailored by an orthodontist.

According to one embodiment, the personalized method of the invention is in view of a few days improvement plan of the alignment of the teeth of a subject, preferably the personalized method of the invention improves the teeth alignment of a subject in a period ranging from 7 days, preferably 1, 2, 3, 4, 5, 6 or 7 days.

According to one embodiment, the personalized method of the invention is in view of a few weeks improvement plan of the alignment of the teeth of a subject, preferably the personalized method of the invention improves the teeth alignment of a subject in a period ranging from 1 to 16 weeks, preferably ranging from 2 to 16 weeks, preferably in 1, 2, 3, 4, 5, 6, 7, 8, 9, 10, 11, 12, 13, 14, 15 or 16 weeks.

According to one embodiment, the personalized method of the invention lasts during a time period ranging from 1 to 16 weeks, preferably, ranging from 1 to 12, more preferably in 1, 2, 3, 4, 5, 6, 7, 8, 9, 10, 11 12, 13, 14, 15 or 16 weeks.

According to one embodiment, the personalized method of the invention comprises a step for analyzing the oral cavity of a subject; preferably for analyzing the initial, actual, updated and/or current state the oral cavity of a subject.

According to one embodiment, the personalized method of the invention comprises a step for analyzing the dentition of a subject; preferably for analyzing the initial, actual, updated and/or current state the dentition of a subject.

Step (i)

According to one embodiment, the method of the invention comprises a step of providing a 2D image or 3D volume (also called 3D image) of the dentition of a subject.

According to one embodiment, the step of providing a 2D image or 3D volume (also called 3D image) of the dentition of a subject, is implemented in the dentist's office or in the orthodontist's office.

According to one embodiment, step (i) is carried out by scanning, directly or indirectly, the dentition of a subject. According to one embodiment, scanning is implemented by optical camera, MRI scanner intra-oral scanner and/or by X-ray scanning machine. According to one embodiment, step (i) comprises collecting the anatomical features of the oral cavity of the subject, preferably by scanning with an intraoral scan and/or X-ray scan of the dentition of the subject. According to one embodiment, the 2D and/or 3D image of the oral cavity including the dentition of the subject, provides the current state of the oral cavity of the subject. According to one embodiment, step (i) is carried out by scanning, one or more teeth of the dentition of the subject. According to one embodiment, step (i) is carried out by scanning the whole tooth or only a part of the tooth, of the subject. According to one embodiment, in the method of the invention, it is not necessary to rescan the patient's dentition during the treatment. According to one embodiment, in the method of the invention, it is not necessary to rescan the whole patient's dentition during the treatment.

According to one embodiment, the current state of the dentition of the subject, is integrated in a patient database combined with an artificial intelligence software, an algorithm, a deep learning process and/or a machine learning process.

According to one embodiment, step (i) further comprises providing a negative mold and/or a positive mold of the dentition of a subject.

According to one embodiment, the positive mold is obtained from a negative mold of the dentition of a subject. According to one embodiment, the negative mold is obtained after dental impression of the dentition of a subject.

According to one embodiment, the material used for dental impression of the dentition of a subject is selected from reversible or irreversible hydrocolloids, elastomers such as silicone elastomers, polyether elastomers, polysulfurised elastomers and their mixtures thereof. According to one embodiment, the material used for dental impression of the dentition of a subject is a polymer or a mixture of polymers, preferably selected form the group of alginate, silicone, polyether and their mixtures thereof. According to one embodiment, the material used for dental impression may comprise pigments.

According to one embodiment, the positive mold is manufactured by casting dental plaster into the negative mold. According to one embodiment, the positive mold is manufactured by casting dental silicone and/or any suitable dental resin in the negative mold.

According to one embodiment, the 3D volume of the dentition of a subject is obtained by scanning a negative mold or a positive mold of the dentition of a subject.

Step (ii)

According to one embodiment, the method of the invention comprises a step of recovering clinical markers of the subject. In the present invention, the terms "clinical markers" relate to any information of the state of a subject comprising the form and/or the size of each tooth of the dentition of the patient (including the crown and/or the root) and optionally including sex, age, anatomical features and/or medical features of said subject. According to one embodiment, the terms "clinical markers" relate to the anatomical features of the oral cavity of the subject such as jaw sizes, the alignment between the lower jaw and the upper jaw, the jaw density, teeth number, the tooth structure including tooth orientation, teeth size, structure of teeth crown and/or structure of teeth root. According to one embodiment, the clinical markers relates to the clinical markers of a state of the subject before wearing the dental aligner manufactured by the method of the invention in course of implementation. According to one embodiment, the clinical markers of the subject at step (ii) define an initial physical state of said subject, preferably an initial physical state of the dentition and/or oral cavity of said subject.

According to one embodiment, the method of the invention comprises a step of recovering the size and/or form of the root teeth of a patient. According to one embodiment, the method of the invention comprises a step of recovering the alveolar bone density of a patient. According to one embodiment, the clinical marker is the bone density, preferably the alveolar bone density, of the dentition of the patient.

According to one embodiment, the clinical markers of the subject, preferably at an initial physical state of said subject, are integrated into a database of patients.

According to one embodiment, the database of patients includes the previous and/or current clinical markers of the subject.

According to one embodiment, the database of patients classifies the patients depending on the same or similar etiology of non-alignment, the same or similar 2D image or 3D volume of the dentition, and/or the same or similar clinical markers. According to one embodiment, the database of patients classifies the patients depending on the same dental treatment goals, preferably depending on the same dental treatment goals given by the practitioner. According to one embodiment, the database of patients further classifies the patients depending on the same or similar evolution of tooth displacement, the same or similar response to the improvement plan and/or the same or similar variation between the actual state and the predicted state of the dentition of the patient.

According to one embodiment, the database of patients comprises suitable information for suggesting an improvement plan for realigning or promoting the realignment of the dentition of a subject in need thereof.

Step (iii)

According to one embodiment, the method of the invention further comprises producing a set of manufacturing parameters of the aligner.

According to one embodiment, step (iii) comprises using an algorithm, a deep learning process and/or a machine learning process. According to one embodiment, step (iii) comprises using an artificial intelligence software. According to one embodiment, when step (i) is carried out by scanning only a part of the tooth of the subject, the algorithm is able to rebuild the virtual image of the whole corresponding tooth, said algorithm being preferably based on the data registered for this subject in the database of patients. According to one embodiment, said database of patients include all data of previous treatment plan complied by the patients and the corresponding results on the non-alignment and the alignment of the dentition of said patients.

According to one embodiment, the practitioner asks the artificial intelligence software, the algorithm, the deep learning or the machine learning to define the best manufacturing parameters of an aligner or a set of aligners, for moving at least one tooth of the current state of the dentition of said subject with a targeted evolution planned in 1, 2, 3, 4, 5, 6, 7, 8, 9, 10, 11, 12, 13, 14, 15 or 16 weeks, and/or depending on the available additive manufacturing technique. According to one embodiment, the practitioner asks the artificial intelligence software, the algorithm, the deep learning or the machine learning to define the best manufacturing parameters of an aligner or a set of aligners, for moving at least one tooth of the current state of the dentition of said subject with a targeted evolution planned in 1, 2, 3, 4, 5, 6 or 7 days, and/or depending on the available additive manufacturing technique.

According to one embodiment, the artificial intelligence software, the algorithm, the deep learning or the machine learning analyses for each subject, the displacement of each tooth of the dentition of the subject between the actual state of the dentition and a previous state of the same dentition and/or a predicted state of the same dentition.

According to one embodiment, the expression "previous state of the dentition" means a state of the dentition of the subject known by the practitioner before the state of the dentition obtained at step (i) of the method of the invention (called "actual state of the dentition"). According to one embodiment, the terms "previous state of the dentition" refer to the state of the dentition of the subject before step i. According to one embodiment, the terms "the data of a previous state of the dentition of the subject" refer to the data dealing with the dentition or a dental treatment plan for the subject, obtained before step i, that-is-to say before providing a 2D image and/or 3D volume showing the actual state of the dentition of the subject. According to one embodiment, the terms "previous state of the dentition" refer to the latest state of the dentition of the subject, before step i.

According to one embodiment, the artificial intelligence software, the algorithm, the deep learning or the machine learning analyses information from the patient database and/or information relative to the current state of the subject in order to classify the non-alignment of the dentition of the subject. According to one embodiment, the artificial intelligence software, the algorithm, the deep learning or the machine learning analyzes the most efficient improvement plan method of the patient database for a short improvement plan of 1, 2, 3, 4, 5, 6, 7, 8, 9, 10, 11, 12, 13, 14, 15 or 16 weeks, preferably depending on the class of the non-alignment of the dentition. According to one embodiment, the artificial intelligence software, the algorithm, the deep learning or the machine learning analyzes the most efficient improvement plan method of the patient database for a short improvement plan of 1,2, 3, 4, 5, 6, 7, 8, 9, 10, 11, 12, 13, 14, 15 or 16 weeks depending on the diagnosis and treatment goals of the practitioner.

According to one embodiment, the artificial intelligence software, the algorithm, the deep learning or the machine learning analyzes the most efficient improvement plan method of the patient database for a short improvement plan of 1, 2, 3, 4, 5, 6 or 7 days, preferably depending on the class of the non-alignment of the dentition. According to one embodiment, the artificial intelligence software, the algorithm, the deep learning or the machine learning analyzes the most efficient improvement plan method of the patient database for a short improvement plan of 1,2, 3, 4, 5, 6 or 7 days depending on the diagnosis and treatment goals of the practitioner.

According to one embodiment, the artificial intelligence software, the algorithm, the deep learning or the machine learning provides manufacturing parameters, preferably optimized manufacturing parameters, for 3D-printing one aligner or a set of aligners for a time period determined by the practitioner, preferably according to the estimated difficulty of the treatment. According to one embodiment, the artificial intelligence software, the algorithm, the deep learning or the machine learning provides manufacturing parameters, preferably optimized manufacturing parameters, for 3D-printing one aligner or a set of aligners for a time period that does not exceed 16 weeks, and for the available additive manufacturing technique. In the present invention, the expression "optimized manufacturing parameters" means that the manufacturing parameters for the (set of) aligner(s) are not only based on the current state of dentition and/or the clinical markers of the subject, but also takes into account relevant information of the patient database for achieving the fastest to a properly aligned dentition.

According to one embodiment, the set of manufacturing parameters are obtained from the 2D image or the 3D image (also called 3D volume) of step (i); from the recovered clinical markers of step (ii) and/or from information issued from a database of patients. According to one embodiment, the set of manufacturing parameters obtained at step (iii) is provided by an artificial intelligence, an algorithm, by deep learning or by machine learning. According to one embodiment, the set of manufacturing parameters obtained by an artificial intelligence, an algorithm, by deep learning or by machine learning, may be modified and/or corrected by the practitioner.

According to one embodiment, the database of patients of step (iii) comprise information of patients having the same or similar etiology of non-alignment, the same or similar 2D image or 3D volume of the dentition, and/or the same or similar clinical markers.

According to one embodiment, the set of manufacturing parameters obtained at step (iii) are selected from physical features of the dental aligner to be manufactured, the printing features including the features of the printing ink, the features of the printing device and the printing parameters.

According to one embodiment, the physical features of the dental aligner comprise the size, the thickness, the density, the roughness, the elasticity, the shape memory, the incorporation of restrain means or means for inducing force level, means for promoting adherence preferably to enamel, and/or the color of said aligner. According to one embodiment, the set of manufacturing parameters includes multiple density values within the same targeted dental aligner. According to one embodiment, the dental aligner includes additives, preferably selected from antibacterial agents, anti-caries agents, and remineralizing agents.

According to one embodiment, the size (length) of the dental aligner ranges from 5 cm to 15 cm, preferably is about 5, 6, 7, 8, 9, 10, 11, 12, 13, 14 or 15 cm.

According to one embodiment, the thickness of the dental aligner ranges from 0.01 cm to 1 cm, preferably is about 0.01; 0.02; 0.03; 0.04; 0.05; 0.06; 0.07; 0.08; 0.09; 0.1; 0.2; 0.3; 0.4; 0.5; 0.6; 0.7; 0.8; 0.9 or 1 cm. According to one embodiment, the thickness of the dental aligner ranges from more than 0 mm to 6 mm, preferably from 0.4 to 1.0 mm. According to one embodiment, the thickness of the dental aligner is about 0.1 mm; 0.2 mm; 0.3 mm; 0.4 mm; 0.5 mm; 0.6 mm; 0.7 mm; 0.8 mm; 0.9 mm; 1 mm; 1.1 mm; 1.2 mm; 1.3 mm; 1.4 mm; 1.5 mm; 1.6 mm; 1.7 mm; 1.8 mm; 1.9 mm; 2 mm; 2.1 mm; 2.2 mm; 2.3 mm; 2.4 mm; 2.5 mm; 2.6 mm; 2.7 mm; 2.8 mm; 2.9 mm; 3 mm; 3.1 mm; 3.2 mm; 3.3 mm; 3.4 mm; 3.5 mm; 3.6 mm; 3.7 mm; 3.8 mm; 3.9 mm; 4 mm; 4.1 mm; 4.2 mm; 4.3 mm; 4.4 mm; 4.5 mm; 4.6 mm; 4.7 mm; 4.8 mm; 4.9 mm; 5.0 mm; 5.1 mm; 5.2 mm; 5.3 mm; 5.4 mm; 5.5 mm; 5.6 mm; 5.7 mm; 5.8 mm; 5.9 mm; or 6.0 mm.

According to one embodiment, the force level of the dental aligner ranges from 0,01 g to 1 kg, preferably is about 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1; 10; 100; 200; 300; 400; 500; 600; 700; 800; 900 or 1000 g.

According to one embodiment, the features of the printing ink comprise its nature and/or its viscosity.

According to one embodiment, the parameters of the printing step comprise the temperature, the pressure, the printing speed and/or the amount of printing ink. According to one embodiment, the parameters of the printing step would be adapted depending on the additive manufacturing technique used in the method of the invention, known by the skilled artisan.

Step (iv)

According to one embodiment, the method of the invention further comprises building up an image of the few week target of improvement of the dentition of the subject. According to one embodiment, the image of improvement is a 1, 2, 3, 4, 5, 6, 7, 8, 9, 10, 11, 12, 13, 14, 15 or 16 weeks target of improvement. According to one embodiment, the image of improvement is a 1, 2, 3, 4, 5, 6 or 7 day target of improvement.

According to one embodiment, the build image of step (iv) integrates the set of manufacturing parameters obtained at step (iii). According to one embodiment, the build image of step (iv) results from the analysis of the information of a database of patients and/or the use of artificial intelligence or any suitable software for providing a dental alignment improvement plan; for example by deep learning or by machine learning. According to one embodiment, the build image of step (iv) results from the analysis of the information of a database of patients and/or the use of an algorithm for providing a dental alignment improvement plan.

According to one embodiment, the build image of step (iv) is a virtual image. According to one embodiment, the build image of step (iv) is a 2D image or a 3D volume of the dentition of the subject.

According to one embodiment, the build image of step (iv) is a virtual image encompassing the final set of manufacturing parameters of the at least one aligner of the improvement plan. According to one embodiment, the at least one aligner of the improvement plan comprises one or more active portions able to apply a displacement force, individualized for each tooth that needs to be realigned, on the dentition of the patient.

According to one embodiment, the active portion has a thickness, a hardness, a surface condition and/or a pressure zone different from those of the main structure of the aligner.

According to one embodiment, the active portion is made in a different material than the main structure of the aligner.

According to one embodiment, the active portion has:
- a thickness ranging from more than 0 mm to 6 mm, preferably from 0.4 to 1 mm,
- a Shore hardness ranging from more than 0 to 100 Shore units,
- a surface condition selected from smooth surface, rough surface and surface comprising dental adhesion means, and/or
- a pressure zone applying a force ranging from more than 0 N·mm to 10 N·mm According to one embodiment, the Shore hardness is determined by the test ASTM D2240. According to one embodiment, the Shore hardness ranges from 1 to 100 Shore units, preferably from 10 to 95 Shore units, more preferably from 35 to 90 Shore units. According to one embodiment, the Shore hardness is about 10, 20, 30, 40, 50, 60, 70, 80 or 90 Shore units.

According to one embodiment, dental adhesion means comprise or consist of any adhesive coating enabling the adhesion of the aligner, preferably of the intrados of the aligner, on the enamel, the dentine or any dental restorative material, According to one embodiment, dental adhesion means include any physical and/or chemical means enabling the adhesion of the aligner on the enamel, the dentine or any dental restorative material of the patient.

Step (v)

According to one embodiment, the method of the invention further comprises manufacturing a dental aligner.

According to one embodiment, manufacturing the dental aligner may be implemented by any suitable techniques known by the skilled artisan, preferably by an additive manufacturing technique or by thermoforming. According to one embodiment, manufacturing the dental aligner is not implemented by thermoforming.

According to one embodiment, 3D printing may be implemented by any additive manufacturing technique known by the skilled artisan including, but not limited to, stereolithography (SLA), fused deposition modeling (FDM), digital light processing (DLP), continuous liquid interface production (CLIP), electron beam melting (EBM), binder jetting (BJ), laminated object manufacturing (LOM) and triple-jetting technology (PolyJet). According to one embodiment, 3D printing is not implemented by fused deposition modeling (FDM).

According to one embodiment, 3D printing may be implemented by any additive manufacturing technique using a polymeric liquid as raw material. According to one embodiment, 3D printing may be implemented by any additive manufacturing technique using polymeric pellets as raw material. According to one embodiment, the method of the invention comprises 3D printing a dental aligner. According to one embodiment, the 3D printing step implies using a printing material selected from printing ink or printing powder.

According to one embodiment, the printing ink and/or the printing powder comprises or consists of at least one polymer and/or monomer and/or at least one metal.

According to one embodiment, the printing ink comprises or consists of a printable material, i.e. a material which is liquid at a temperature ranging from −30° C. to 300° C.; preferably from −20° C. to 300° C., −20° C. to 300° C., −20° C. to 300° C., −20° C. to 300° C., −20° C. to 300° C., −10° C. to 300° C., 0° C. to 300° C., −10° C. to 300° C., 20° C. to 300° C., 30° C. to 300° C., 40° C. to 300° C., 50° C. to 300° C., 60° C. to 300° C., 70° C. to 300° C., 80° C. to 300° C., 90° C. to 300° C., 100° C. to 300° C., 110° C. to 300° C., 120° C. to 300° C., 130° C. to 300° C., 140° C. to 300° C., 150° C. to 300° C., 160° C. to 300° C., 170° C. to 300° C., 180° C. to 300° C., 190° C. to 300° C., 200° C. to 300° C., 210° C. to 300° C., 220° C. to 300° C., 230° C. to 300° C., or 230° C. to 300° C.; preferably from −20° C. to 290° C., −20° C. to 280° C., −20° C. to 270° C., −20° C. to 260° C., −20° C. to 250° C., 30° C. to 240° C., −30° C. to 230° C., −30° C. to 220° C., −30° C. to 210° C., −30° C. to 200° C., −30° C. to 190° C., −30° C. to 180° C., −30° C. to 170° C., −30° C. to 160° C., −30° C. to 150° C., −30° C. to 140° C., −30° C. to 130° C., −30° C. to 120° C., −30° C. to 110° C., −30° C. to 100° C., −30° C. to 90° C., −30° C. to 80° C., −30° C. to 70° C., −30° C. to 60° C., −30° C. to 50° C., −30° C. to 40° C., −30° C. to 30° C., −30° C. to 20° C., −30° C. to 10° C., or −30° C. to 0° C.

According to one embodiment, the printing ink and/or the printing powder comprises or consists of a polymer or a mixture of polymer selected from: polyurethanes (TPU), polyamides, polyesters or co-polyesters such as PETG, polycarbonates, polymethacrylates such as polymethylmethacrylate (PMMA), polyacrylates, polyolefins such as polypropylene or polyethylene, polyether sulfones (PES) and any mixture thereof.

According to one embodiment, the printing ink and/or the printing powder is a biocompatible material. According to one embodiment, the printing ink and/or the printing powder comprises filler materials such as inorganic fillers and organic fillers, preferably pigments. According to one embodiment, the printing ink and/or the printing powder comprises catalysts, stabilizers, plasticizers, fibers or their combinations.

According to one embodiment, the printing ink comprises at least one initiator, preferably a photoinitiator and/or a thermoinitiator known by the skilled artisan. Non-limited examples of photoinitiators comprise methylbenzoylformate, 1-hydroxycyclohexylphenylketone, 2-hydroxy-2-methylpropiophenone, phenylbis(2,4,6-trimethylbenzoyl) phosphine oxide, diphenyl(2,4,6-trimethylbenzoyl) phosphine oxide, 2,2-dimethoxy-2-phenylacetophenone, and benzophenone.

Non-limited examples of thermoinitiators comprise azoics such as 4,4'-azobis(4-cyanovaleric) acid, 1,1'-azobis (cyclohexanecarbonitrile), 2,2'-azobisisobutyronitrile, 2,2'-azobis(2-methylpropionitrile; peroxides such as benzoyl peroxide, 1,1-bis(tert-butylperoxy)cyclohexane, 2,5-bis (tert-butylperoxy)-2,5-dimethylhexane, tert-butyl hydroperoxide, tert-butyl peroxide, tert-butyl peroxybenzoate, lauroyl peroxide; and peracetates such as tert-butyl peracetate.

According to one embodiment, when the additive manufacturing technique requires that the starting material is under powder form, the particles size of said powder ranges from 20 to 100 µm; preferably from 30 to 100 µm, from 40 to 100 µm, from 50 to 100 µm, from 60 to 100 µm, from 70 to 100 µm, from 80 to 100 µm, or from 90 to 100 µm; preferably from 20 to 90 µm, from 20 to 80 µm, from 20 to 70 µm, from 20 to 60 µm, from 20 to 50 µm, from 20 to 40 µm, or from 20 to 30 µm. According to one embodiment, when the additive manufacturing technique requires that the starting material is under powder form, the particles size of said powder is about 20, 30, 40, 50, 60, 70, 80, 90, or 100 µm.

According to one embodiment, the printing powder is selected from polymers, monomers and metals. According to one embodiment, metals are preferably selected from aluminum, steel, brass, copper, bronze, silver, gold, platinum, titanium and theirs mixtures.

According to one embodiment, manufacturing the dental aligner may be implemented by first providing a positive mold of the build image obtained at step (iv) and then, thermoforming the dental aligner on said positive mold.

According to one embodiment, 3D printing step does not comprise using a positive mold of the build image obtained at step (iv). According to one embodiment, 3D printing step does not comprise using any positive mold as support for 3D printing the dental aligner of the invention.

According to one embodiment, 3D printing step comprises using a positive mold of the build image obtained at step (iv). According to one embodiment, 3D printing step comprises using a positive mold of the build image obtained at step (iv), as support for 3D printing the dental aligner of the invention. According to one embodiment, the positive mold of the build image obtained at step (iv) is obtained itself by 3D printing. According to one embodiment, the positive mold of the build image obtained at step (iv) is obtained by thermoforming.

According to one embodiment, 3D printing step comprises using a negative mold of the build image obtained at step (iv). According to one embodiment, 3D printing step comprises using a negative mold of the build image obtained at step (iv), as support for 3D printing the dental aligner of the invention. According to one embodiment, the negative mold of the build image obtained at step (iv), is obtained itself by 3D printing. According to one embodiment, the negative mold of the build image obtained at step (iv) is obtained by thermoforming.

According to one embodiment, 3D printing step is implemented to a temperature ranging from −30° C. to 250° C.; preferably from −20° C. to 250° C., −10° C. to 250° C., 0° C. to 250° C., −10° C. to 250° C., 20° C. to 250° C., 30° C. to 250° C., 40° C. to 250° C., 50° C. to 250° C., 60° C. to 250° C., 70° C. to 250° C., 80° C. to 250° C., 90° C. to 250° C., 100° C. to 250° C., 110° C. to 250° C., 120° C. to 250° C., 130° C. to 250° C., 140° C. to 250° C., 150° C. to 250° C., 160° C. to 250° C., 170° C. to 250° C., 180° C. to 250° C., 190° C. to 250° C., 200° C. to 250° C., 210° C. to 250° C., 220° C. to 250° C., 230° C. to 250° C., or 230° C. to 250° C.; preferably from −30° C. to 240° C., −30° C. to 230° C., −30° C. to 220° C., −30° C. to 210° C., −30° C. to 200° C., −30° C. to 190° C., −30° C. to 180° C., −30° C. to 170° C., −30° C. to 160° C., −30° C. to 150° C., −30° C. to 140° C., −30° C. to 130° C., −30° C. to 120° C., −30° C. to 110° C., −30° C. to 100° C., −30° C. to 90° C., −30° C. to 80° C., −30° C. to 70° C., −30° C. to 60° C., −30° C. to 50° C., −30° C. to 40° C., −30° C. to 30° C., −30° C. to 20° C., −30° C. to 10° C., or −30° C. to 0° C.

According to one embodiment, the print speed depends on the additive manufacture technique used. According to one embodiment, 3D printing step is implemented at a print speed ranging from more than 0 mm/h to 200 mm/h, preferably for SLS, SLA or FDM technique. According to one embodiment, 3D printing step is implemented at a print speed ranging from 10 mm/h to 200 mm/h, preferably from 20 mm/h to 200 mm/h, 20 mm/h to 200 mm/h, 30 mm/h to 200 mm/h, 40 mm/h to 200 mm/h, 50 mm/h to 200 mm/h, 60 mm/h to 200 mm/h, 70 mm/h to 200 mm/h, 80 mm/h to 200 mm/h, 90 mm/h to 200 mm/h, 100 mm/h to 200 mm/h, 110 mm/h to 200 mm/h, 120 mm/h to 200 mm/h, 130 mm/h to 200 mm/h, 140 mm/h to 200 mm/h, 150 mm/h to 200 mm/h, 160 mm/h to 200 mm/h, 170 mm/h to 200 mm/h, 180 mm/h to 200 mm/h, or 190 mm/h to 200 mm/h; preferably from 10 mm/h to 190 mm/h, 10 mm/h to 180 mm/h, 10 mm/h to 170 mm/h, 10 mm/h to 160 mm/h, 10 mm/h to 150 mm/h, 10 mm/h to 140 mm/h, 10 mm/h to 130 mm/h, 10 mm/h to 120 mm/h, 10 mm/h to 110 mm/h, 10 mm/h to 100 mm/h, 10 mm/h to 90 mm/h, 10 mm/h to 80 mm/h, 10 mm/h to 70 mm/h, 10 mm/h to 60 mm/h, 10 mm/h to 50 mm/h, 10 mm/h to 40 mm/h, 10 mm/h to 30 mm/h, or 10 mm/h to 20 mm/h. According to one embodiment, 3D printing step is implemented at a print speed of about 5, 10, 15, 20, 25, 30, 35, 40, 45, 50, 55, 60, 65, 70, 75, 80, 85, 90, 95, 100, 110, 120, 130, 140, 150, 160, 170, 180, 190 or 200 mm/h.

According to one embodiment, 3D printing step is implemented at a print speed ranging from more than 0 $mm^3/s$ to 20 $mm^3/s$, preferably for DMLS technique. According to one embodiment, 3D printing step is implemented at a print speed ranging from 1 $mm^3/s$ to 20 $mm^3/s$, preferably 2, 3, 4, 5, 6, 7, 8, 9, 10, 11, 12, 13, 14, 15, 16, 17, 18, 19 or 20 $mm^3/s$.

According to one embodiment, 3D printing step is implemented during a time period depending on the additive manufacturing technique and its experimental parameters (such as print speed, printing material, etc. . . .). According to one embodiment, 3D printing step is implemented during a time period ranging from more than 1 min to 1440 min, preferably from 1 min to 1390 min, 1 min to 1320 min, 1 min to 1260 min, 1 min to 1200 min, 1 min to 1140 min, 1 min to 1080 min, 1 min to 1020 min, 1 min to 960 min, 1 min to 900 min, 1 min to 780 min, 1 min to 720 min, 1 min to 660 min, 1 min to 600 min, 1 min to 540 min, 1 min to 480 min, 1 min to 420 min, 1 min to 360 min, 1 min to 300 min, 1 min to 240 min, 1 min to 180 min, 1 min to 120 min, 1 min to 60 min, 1 min to 50 min, 1 min to 40 min, 1 min to 30 min, 1 min to 20 min, or 1 min to 10 min. According to one embodiment, 3D printing step is implemented during a time period ranging from 5, 10, 15, 20, 25, 30, 35, 40, 45, 50, 55 or 60 min.

According to one embodiment, the method of the invention comprises:
i. providing a 2D image and/or 3D volume of the dentition of a subject showing a non-alignment of its dentition;
ii. recovering clinical markers of the subject, including age, sex, anatomical features;
iii. producing an initial set of manufacturing parameters of the aligner from the image or the volume, from the recovered clinical markers, and from information issued from a database of patients having same or similar etiology of non-alignment, same or similar image or, same or similar clinical markers;
iv. building up an image the 1-7 day target of improvement; and
v. 3D printing, directly or indirectly, of the at least one aligner.

According to one embodiment, the method of the invention comprises:
i. providing a 2D image and/or 3D volume of the dentition of a subject showing a non-alignment of its dentition;
ii. recovering clinical markers of the subject, including age, sex, anatomical features;

iii. producing an initial set of manufacturing parameters of the aligner from the image or the volume, from the recovered clinical markers, and from information issued from a database of patients having same or similar etiology of non-alignment, same or similar image or, same or similar clinical markers;

iv. building up an image the 1-16 week target of improvement, preferably 1-12 week target of improvement, more preferably 3-12 weeks improvement; and v. 3D printing, directly or indirectly, of the at least one aligner.

According to one embodiment, when the method of the invention is implemented by a practitioner during a consultation, the practitioner may choose for 3D-printing one aligner for less than one-week improvement plan, preferably less than 7 days, less than 6 days, or less than 5 days.

According to one embodiment, when the method of the invention is implemented by a practitioner during a consultation, the practitioner may choose for 3D-printing one aligner for a 1-, 2- or 3-weeks improvement plan or a set of aligners for an improvement plan lasting from higher than 1 week, preferably higher than 2 weeks but that does not exceed 16 weeks.

According to one embodiment, at the beginning of the method of the invention, the dentition of the subject is not properly aligned. According to one embodiment, at the end of the method of the invention, the dentition alignment of the subject has not changed or has changed so that the dentition is partially or totally properly aligned. According to one embodiment, the method of the invention can be repeated as many times as necessary until a perfect alignment of the patient's dentition is achieved.

Advantageously, the method of the invention provides a more reliable method of manufacturing a set of aligners, taking into account the evolution of a subject's dentition over time, particularly over a period of 1 to 16 weeks, particularly over a period of 1 to 12 days, more particularly over a period of 1 to 7 days.

Advantageously, the method of the invention may be directly implemented by the practitioner, preferably on the time of a consultation.

Advantageously, the method of the invention avoids the impression of a large number of aligners on an improvement plan period. Especially, the method of the invention reduces the number of aligners needed in an improvement plan for alignment of the dentition of a subject. Advantageously, the method of the invention reduces the time needed for aligning the dentition of a subject.

Dental Aligner

The invention also concerns a dental aligner or a set of aligners, preferably obtainable by the method of the invention.

According to one embodiment, the dental aligner comprises means for applying at least one displacement force in order to realigned the dentition of a patient. According to one embodiment, the dental aligner comprises means for applying a displacement force that is individualized for each tooth that needs to be realigned over the treatment period.

According to one embodiment, means for applying a displacement force comprise or consist of physical and/or chemical means. According to one embodiment, means for applying a displacement force comprise or consist of the presence on the aligner, of at least one active portion.

According to one embodiment, the active portion has:
a thickness ranging from more than 0 mm to 6 mm, preferably from 0.4 to 1 mm, more preferably is 0.5; 0.6 or 0.7 mm.
a Shore hardness ranging from more than 0 to 100 Shore units,
an elastic modulus ranging from more than 0 to 2500 MPa, determined by the test ASTM 638-2010,
a flexural modulus ranging from more than 0 to 2000 MPa, determined by the test ISO 178,
a surface condition selected from smooth surface, rough surface and surface comprising dental adhesion means, and/or
a pressure zone applying a force ranging from more than 0 N·mm to 10 N·mm According to one embodiment, the thickness of the active portion ranges from more than 0 mm to 6 mm. According to one embodiment, the thickness of the active portion is 0.1 mm; 0.2 mm; 0.3 mm; 0.4 mm; 0.5 mm; 0.6 mm; 0.7 mm; 0.8 mm; 0.9 mm or 1 mm.

According to one embodiment, the dental aligner is made of at least two different materials.

According to one embodiment, the elastic modulus ranges from 10 to 2500 MPa, preferably is about 100, 200, 300, 400, 500, 600, 700, 800, 900, 1000, 1100, 1200, 1300, 1400, 1500, 1600, 1700, 1800, 1900, 2000, 2100, 2200, 2300, 2400 or 2500 MPa.

According to one embodiment, the flexural modulus ranges from 10 to 2000 MPa, preferably is about 100, 200, 300, 400, 500, 600, 700, 800, 900, 1000, 1100, 1200, 1300, 1400, 1500, 1600, 1700, 1800, 1900 or 2000 MPa.

According to one embodiment, the pressure zone applied a force ranging from 0.1 N·mm to 9 N·mm. According to one embodiment, the pressure zone applies a force of about 0.1; 0.2; 0.3; 0.4; 0.5; 0.6; 0.7; 0.8; 0.9; 1; 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9; 5; 5.1; 5.2; 5.3; 5.4; 5.5; 5.6; 5.7; 5.8; 5.9; 6; 6.1; 6.2; 6.3; 6.4; 6.5; 6.6; 6.7; 6.8; 6.9; 7; 7.1; 7.2; 7.3 ;7.4; 7.5; 7.6; 7.7; 7.8; 7.9; 8; 8.1; 8.2; 8.3; 8.4; 8.5; 8.6; 8.7; 8.8; 8.9 or 9 N·mm.

According to one embodiment, the dental aligner is suitable for children, teenagers and/or adults.

According to one embodiment, the dental aligner is suitable for any orthodontic pathology. According to one embodiment, the dental aligner is suitable for a prognathous subject. According to one embodiment, the dental aligner is suitable for a retrognathous subject.

According to one embodiment, the dental aligner further comprises one or more fake teeth. According to one embodiment, the dental aligner is transparent or colored of the dentition color of said patient, on the area of the dental aligner comprising the fake tooth or fake teeth. According to one embodiment, the dental aligner simulates the presence of false teeth.

According to one embodiment, the dental aligner is colored, preferably of the color of the dentition of the subject. According to one embodiment, the dental aligner is transparent.

According to one embodiment, the dental aligner comprises an active part able to apply a force level on at least one tooth of the dentition of the subject.

According to one embodiment, the active part is a thicker part of the dental aligner and/or is a part of the dental aligner comprising means of restraint.

According to one embodiment, means of restraint of the dental aligner are selected from thicker areas, rough areas, elastic areas, shape memory parts, adhesive parts, multiple densities parts, brackets and any combinations thereof. According to one embodiment, the dental aligner comprises areas of extra thickness in the aligner's intrados.

According to one embodiment, the set of the aligners preferably obtainable by the method of the invention fit with the dentition evolution of the subject on a time period ranging from 1 to a time period estimated by the practitioner, preferably from 1 to 16 weeks, preferably from 1 to 7 days. According to one embodiment, the set of the aligners preferably obtainable by the method of the invention fit with the dentition evolution of the subject on a time period ranging from 1 to 16 weeks, preferably from 3 to 16 weeks, more preferably from 3 to 12 weeks, even more preferably from 1 to 7 days.

Uses

The invention also concerns the dental aligner of the invention for use in a 1-16 weeks treatment, preferably a 3-16 weeks treatment, more preferably a 3-12 weeks treatment, even more preferably from 1-7 days treatment of non-alignment of the teeth of a subject.

According to one embodiment, the dental aligner of the invention is useful for treating any orthodontic pathologies, preferably for any orthodontic pathologies known by the practitioner such as Class I, Class II or Class III of orthodontic pathologies.

According to one embodiment, the dental aligner of the invention is useful for treating dento-maxillary disharmony including for example, inverted posterior unilateral posterior, bilateral posterior, overlap, overhanging, open bite, endoalveolina, dental-dental disharmony, endomaxillary, or skeletal slices.

According to one embodiment, the present invention refers to a method for treating a non-alignment of the teeth of a subject, said method comprising using at least one dental aligner of the invention.

According to one embodiment, the present invention refers to a method for treating a non-alignment of the teeth of a subject, comprising:
 (a) Providing at least one aligner according to the method as defined above; and
 (b) Wearing the at least one aligner over a treatment period ranging from 1 to 16 weeks.

According to one embodiment, the method of the invention is repeated until complete alignment of the dentition of the subject.

EXAMPLES

The present invention is further illustrated by the following examples.

The method of the invention is implemented in a practitioner as follows.

A dentist or orthodontist examines a subject with a non-aligned dentition: either the dentition of said subject has never been treated for alignment, or the dentition of said subject has been previously treated with aligner and/or other means for dentition alignment such as dental braces for example. The practitioner records patient information including sex, age, anatomical features comprising jaw sizes, the alignment between the lower jaw and the upper jaw, the jaw density, teeth number, the tooth structure, teeth size, structure of teeth crown, and/or structure of teeth root; and/or etiology of the non-alignment dentition.

For helping the practitioner to collect the anatomical features of the oral cavity of the subject, the practitioner scans with an intraoral scan and/or X-ray scan of the dentition of the subject. A 2D and/or 3D image of the oral cavity including the dentition of the subject is provided of the current state of the dentition of the subject.

This current state defined by the patient information as mentioned hereinabove, is integrated in a patient database combined with an artificial intelligence software, an algorithm, by deep learning or by machine learning.

In view of the treatment goals defined by the practitioner, the practitioner asks the artificial intelligence software, an algorithm, by deep learning or by machine learning, to define the best manufacturing parameters of an aligner or a set of aligners, for moving at least one tooth of the current state of the dentition of said subject with a targeted evolution planned in 1, 2, 3, 4, 5, 6, 7, 8, 9, 10, 11, 12, 13, 14, 15 or 16 weeks, or planned in 1, 2, 3, 4, 5, 6 or 7 days, and depending on the available additive manufacturing technique.

Alternatively, the practitioner asks the artificial intelligence software, the algorithm, the deep learning software or the machine learning software, to define only a part of the best manufacturing parameters of an aligner or a set of aligners for moving at least one tooth of the current state of the dentition of said subject with a targeted evolution planned in 1, 2, 3, 4, 5, 6, 7, 8, 9, 10, 11, 12, 13, 14, 15 or 16 weeks, or planned in 1, 2, 3, 4, 5, 6 or 7 days, and depending on the available additive manufacturing technique.

For answering to the practitioner, first, the artificial intelligence software, the algorithm, the deep learning software or the machine learning software both analyses information from the patient database and information relative to the current state of the subject in order to classify the non-alignment of the dentition of the subject. Second, depending on the class of the non-alignment of the dentition, all data of said patient (including the size and the form of each tooth (crown and/or root), bone density, etc.) collected at the beginning and during the treatment and the targeted treatment goals given by the practitioner, the AI software, the algorithm, the deep learning software or the machine learning software analyzes the most efficient improvement plan method of the patient database for a short improvement plan of 1, 2, 3, 4, 5, 6, 7, 8, 9, 10, 11, 12, 13, 14, 15 or 16 weeks; or 1, 2, 3, 4, 5, 6 or 7 days.

Finally, the AI software the algorithm, the deep learning software or the machine learning software provides to the practitioner the optimized manufacturing parameters for 3D-printing one aligner or a set of aligners for a time period that does not exceed 12 weeks, and for the available additive manufacturing technique. The AI software, the algorithm, the deep learning software or the machine learning software also provides to the practitioner, a virtual 3D image of the targeted dentition ("predicted state of the dentition") of the patient (i.e. a partially and/or totally aligned dentition) based on the optimized manufacturing parameters as obtained above.

During the consultation, the practitioner may choose for 3D-printing one aligner for a 1- or 2-weeks improvement plan or a set of aligners for an improvement plan lasting from higher than 2 weeks but that does not exceed 16 weeks.

The invention claimed is:
1. A method for providing at least one dental aligner comprising means for applying a displacement force, identical or different, on each tooth of the dentition of a patient; said method being with reference to an actual state of the dentition of the patient and in view of an improvement plan of the alignment targeted over a period of time ranging from 1 to 16 weeks, of the teeth of a subject, said method comprising:
   i. providing a 2D image and/or 3D volume of the actual state of the dentition of a subject showing a non-alignment of its dentition;
   ii. recovering clinical markers of the subject comprising the form and/or size of the dental root and/or the crown for each tooth of the dentition and one or more of further clinical markers of the subject selected from age, sex, dental disease, and anatomical features;
   iii. producing an initial set of manufacturing parameters of the at least one aligner from:
      the 2D image and/or the 3D volume of the actual state of the dentition of the subject, and its comparison with the 2D image and/or the 3D volume of a previous state of the dentition of the subject and/or with the 2D image and/or the 3D volume of a predicted state of the dentition of the subject,
      the recovered clinical markers of step ii, and
      information issued from a database of patients having same or similar etiology of non-alignment, same or similar 2D image and/or 3D volume in a previous state, same or similar evolution of tooth displacement or response to the improvement plan, same or similar clinical markers;
   iv. building up a 3D volume of the improvement plan from the initial set of manufacturing parameters obtained from step iii, leading to a final set of manufacturing parameters of the at least one aligner for a treatment period ranging from 1 to 16 weeks, said final set of manufacturing parameters comprising:
      a thickness ranging from 0.3 mm to 6 mm,
      a Shore hardness ranging from more than 0 to 100 Shore units,
      a surface condition selected from smooth surface, rough surface, and surface comprising dental adhesion means, and/or
      a pressure zone applying a force ranging from more than 0 N·mm to 10 N·mm; and
   v. directly 3D printing of the at least one aligner;
wherein the whole method is implemented during a dental visit.

2. The method according to claim 1, wherein the 2D image and/or 3D volume of the dentition of a subject is achieved by directly scanning the dentition of the subject.

3. The method according to claim 2, wherein the scanning is implemented by optical camera, MRI scanner, X-ray machine, or intra-oral scanner.

4. The method according to claim 1, wherein the anatomical features are selected from jaw sizes, the alignment between the lower jaw and the upper jaw, jaw density, tooth number, tooth structure, and/or structure of the tooth crown.

5. The method according to claim 1, wherein the clinical markers further include the bone density of the dentition of the patient.

6. The method according to claim 1, wherein producing an initial set of manufacturing parameters and/or building up a 3D volume of the improvement plan, is/are achieved by an artificial intelligence software, a deep learning software, or a machine learning software.

7. The method according to claim 1, wherein the final set of manufacturing parameters of the at least one aligner further comprises one or more parameters selected from: the size, the density, and/or the color of said at least one aligner; the temperature, the pressure, and/or the printing speed of a 3D printing device used for the 3D printing of the at least one aligner; and/or the nature, the viscosity and/or the amount of printing ink of the 3D printer.

8. The method according to claim 1, wherein 3D printing of the at least one aligner is achieved by stereolithography (SLA), fused deposition modeling (FDM), pellet additive manufacturing (PAM), digital light processing (DLP), continuous liquid interface production (CLIP), electron beam melting (EBM), binder jetting (BJ), laminated object manufacturing (LOM), or triple-jetting technology (PolyJet).

9. The method according to claim 1, wherein the 2D image and/or 3D volume of the dentition of a subject is achieved by scanning a positive mold or a negative mold of the dentition of the subject.

10. The method according to claim 1, wherein step i further comprises directly scanning the dentition of the subject with an optical camera, MRI scanner, intraoral scanner, and/or X-ray machine to provide the 2D image and/or 3D volume.

* * * * *